(12) United States Patent
Chong

(10) Patent No.: US 11,260,207 B2
(45) Date of Patent: Mar. 1, 2022

(54) CATHETER VALVE

(71) Applicant: Kim Seng Chong, Kedah (MY)

(72) Inventor: Kim Seng Chong, Kedah (MY)

(*) Notice: Subject to any disclaimer, the term of this patent is extended or adjusted under 35 U.S.C. 154(b) by 0 days.

(21) Appl. No.: 16/065,337

(22) PCT Filed: May 16, 2018

(86) PCT No.: PCT/MY2018/050031
§ 371 (c)(1),
(2) Date: Jun. 22, 2018

(87) PCT Pub. No.: WO2019/221592
PCT Pub. Date: Nov. 21, 2019

(65) Prior Publication Data
US 2021/0060314 A1 Mar. 4, 2021

(30) Foreign Application Priority Data
May 14, 2018 (MY) .......................... PI 2018000743

(51) Int. Cl.
A61M 25/10 (2013.01)

(52) U.S. Cl.
CPC ............ A61M 25/10186 (2013.11); A61M 2025/1043 (2013.01); A61M 2205/0216 (2013.01)

(58) Field of Classification Search
CPC ............ A61M 39/22; A61M 25/10186; A61M 2039/2493; A61M 2039/267–268; A61M 25/10185; A61M 25/1025
See application file for complete search history.

(56) References Cited

U.S. PATENT DOCUMENTS 5,047,021 A * 9/1991 Utterberg ............... F16L 33/24
604/533
5,049,128 A * 9/1991 Duquette ............. A61M 39/02
604/83
(Continued)

FOREIGN PATENT DOCUMENTS

MY 141510 A 5/2010

OTHER PUBLICATIONS

International Preliminary Report on Patentability received for PCT Patent Application No. PCT/MY2018/050031, dated Nov. 17, 2020, 6 pages.
(Continued)

Primary Examiner — Nathan R Price
Assistant Examiner — Melissa A Snyder
(74) Attorney, Agent, or Firm — Workman Nydegger

(57) ABSTRACT

The present invention relates to a catheter valve for use with a catheter. The catheter valve comprises an inlet nozzle at a front end of the valve and an outlet nozzle at a rear end of the valve. The valve comprises a longitudinal stem encapsulated within a middle section of the valve which extends in between the front end and the rear end of the valve. The longitudinal stem is divided into a front end and a rear end by a rib and an O-ring is inserted into the front end of the stem; and a resilient means is inserted into the rear end of the stem; the front end of the longitudinal stem further comprises sectional longitudinal grooves which cuts across the longitudinal and cylindrical stem extending from a head end of the front end of the stem up till the rib of the stem and the head end is curved inwardly in between each sectional longitudinal groove; and the rear end of the longitudinal stem further comprises sectional longitudinal grooves which cuts across the longitudinal and cylindrical stem in a trian-
(Continued)

gular form extending from a head end of the rear end of the stem up till a bottom interface of the rib.

13 Claims, 2 Drawing Sheets

(56) References Cited

U.S. PATENT DOCUMENTS

| | | | | |
|---|---|---|---|---|
| 6,029,946 | A * | 2/2000 | Doyle | A61M 39/26 251/149.1 |
| 6,228,069 | B1 * | 5/2001 | Barth | A61M 39/26 604/249 |
| 6,540,205 | B1 * | 4/2003 | Stafford | F16K 1/50 251/205 |
| 2010/0263733 | A1 | 10/2010 | Klecker et al. | |
| 2014/0296794 | A1 | 10/2014 | Li | |

OTHER PUBLICATIONS

International Search Report and Written Opinion received for PCT Patent Application No. PCT/MY2018/050031, dated Mar. 25, 2019, 8 pages.

* cited by examiner

CATHETER VALVE

FIELD OF INVENTION

The present invention relates to a catheter valve for use with a catheter. The catheter valve comprises an inlet nozzle at a front end of the valve and an outlet nozzle at a rear end of the valve. In particular, the valve comprises a longitudinal stem encapsulated within a middle section of the valve extending in between the front end and the rear end of the valve. The structural configuration of the longitudinal stem facilitates rapid inflation and deflation of an inflatable balloon at a distal end of the catheter during catheterization.

BACKGROUND ART

Restriction of air and fluid flow is observed in inflation and deflation during catheterization procedure with the use of medical valves. The present invention is an improvement of the Patent No. MY-141510-A entitled "Medical Check Valve" having a grant date of 14 May 2010 and a filing date of 7 Jun. 2002. In particular, the structural configuration of the longitudinal stem of the valve of the present invention facilitates rapid inflation and deflation of an inflatable balloon at a distal end of the catheter during catheterization.

An example of a catheter with a detachable hub is disclosed in Canada Patent Publication No. CA 2778799 A1 having a filing date of 24 Apr. 2012 entitled "Balloon Catheter with Detachable Hub, and Methods for Same" (hereinafter referred to as "the CA 799 Publication") (Applicant: Cook Medical Technologies LLC US). The CA 799 Publication provides a balloon catheter comprising a distal anchoring balloon; a proximal hub that is removable from the catheter body; and a valve structure to maintain said balloon in inflated state and after removal of the proximal hub. The balloon catheter of the CA 799 Publication is configured for passage through an ultra-slim endoscope.

Another example for infusion systems and connectors utilized with catheter devices is disclosed in International Patent Application Publication No. WO 2017/042359 A1 having a filing date of 9 Sep. 2016 entitled "Infusion Systems, Connectors for Use with Catheter Devices, and Related Methods" (hereinafter referred to as "the WO 359 Publication") (Applicant: B Braun Melsungen AG). The WO 359 Publication provides intravenous infusion devices comprising Intravenous (IV) catheters and connector specifically male Luer connector of IV administration set for IV extension lines. The IV catheters hub is part of the catheter assembly with a needle, needle hub, valve, valve opener and a needle guard.

A further example of catheters inserted with valve is disclosed in United States Patent Publication No. US 2017/0259045 A1 having a filing date of 30 Mar. 2017 entitled "Stretch Valve Balloon Catheter and Methods for Producing and Using Same" (hereinafter referred to as "the US 045 Publication") (Applicant: Mayser LLC). The US 045 Publication provides an automatic deflating balloon catheter with a stretch valve and method for using and manufacturing said catheter. The stretch valve has a hollow base fixed in the second lumen at the proximal catheter end and allows a fluid therethrough and a hollow plug slidably positioned in the second lumen in a steady state prevent inflation fluid from passing through the drainage port, and when actuated, slide within the second lumen to permit inflation fluid to pass through the drainage port and into second lumen.

Due to the restrictions on the currently available medical valves specifically catheter valves for use with a catheter, there is a need to improve the structural configuration of the catheter valve to obtain rapid inflation and deflation of an inflatable balloon at a distal end of the catheter during catheterization procedure.

SUMMARY OF INVENTION

The present invention relates to a catheter valve for use with a catheter. The catheter valve (100) comprising an inlet nozzle (102a) at a front end (102) of the valve (100) and an outlet nozzle (112b) at a rear end of the valve (100). In particular, the valve comprises a longitudinal stem (108) encapsulated within a middle section (102b) of the valve (100) extending in between the front end (102) and the rear end (112) of the valve. The structural configuration of the longitudinal stem facilitates rapid inflation and deflation of an inflatable balloon at a distal end of the catheter during catheterization.

One aspect of the invention provides a catheter valve (100) for use with a catheter. The catheter valve (100) comprising an inlet nozzle (102a) at a front end (102) of the valve (100) for receiving a syringe to facilitate rapid inflation and deflation of an inflatable balloon at a distal end of the catheter during catheterization; an outlet nozzle (112b) at a rear end (112) of the valve (100) being inserted into one of the catheter's lumen enabling inflation and deflation of the inflatable balloon of the catheter during catheterization; and a longitudinal stem (108) encapsulated within a middle section (102b) of the valve (100) extending in between the front end (102) and the rear end (112) of the valve; the longitudinal stem (108) is divided into a front end (108b) and a rear end (108c) by a rib (108a); an O-ring (106) is inserted into the front end (102) of the stem enabling the O-ring (106) to be seated in a groove and compressed during assembly between the front end (108b) and the rear end (102) of the valve (100) creating a seal at a top interface of the rib (108a); and a resilient means (110) is inserted into the rear end (108c) of the stem (108). The front end (108b) of the longitudinal stem (108) further comprises sectional longitudinal grooves which cuts across the longitudinal and cylindrical stem extending from a head end of the front end of the stem up till the rib (108a) of the stem and the head end is curved inwardly in between each sectional longitudinal groove; and the rear end (108c) of the longitudinal stem (108) further comprises sectional longitudinal grooves which cuts across the longitudinal and cylindrical stem (108) in a triangular form (108d) extending from a head end of the rear end (108c) of the stem up till a bottom interface of the rib (108a).

Preferably, the front end (108b) of the longitudinal stem (108) is half of a length of the rear end (108c) of the longitudinal stem (108).

Another aspect of the invention provides that the inlet nozzle (102a) at a front end (102) of the valve is smaller in diameter at a front opening of a proximal end of the inlet nozzle with a larger diameter towards a rear opening of a distal end of the inlet nozzle (102a).

Yet another aspect of the invention provides that the front opening of a proximal end of the inlet nozzle (102a) and the rear opening of a distal end of the inlet nozzle with a change of diameter there between forms a seat which engages the head end of the front end (108b) of the longitudinal stem (108) up till the rib (108a) with the front end (108b) of the longitudinal stem (108) protrudes out of the seat and the rib (108a) resting at the bottom interface of the seat.

Still another aspect of the invention provides that the front opening of the rear end (112) of the valve (100) with a change of diameter there between forms a seat which engages the head end of the rear end (108c) of the stem with the head end of the rear end (108c) of the stem resting on an interface in a middle of the internal rear end (112) of the valve.

Another aspect of the invention provides that resilient means (110) includes a spring, and any other elastic material which provides compressibility.

A further aspect of the invention provides that the catheter valve (100) is detachable between the front end and the rear end of the valve (100).

Still another aspect of the invention provides that the catheter valve (100) comprises of a two part assembly with a first part of the assembly comprising the front end (102) and the middle section of the valve and a second part of the assembly comprising the rear end (112) of the valve with the outlet nozzle (112b).

Yet another aspect of the invention provides that O-ring (106) is made of rubber, silicone or any material which enables formation of a seal.

The present invention consists of features and a combination of parts hereinafter fully described and illustrated in the accompanying drawings, it being understood that various changes in the details may be made without departing from the scope of the invention or sacrificing any of the advantages of the present invention.

BRIEF DESCRIPTION OF ACCOMPANYING DRAWINGS

To further clarify various aspects of some embodiments of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the accompanying drawings.

DETAILED DESCRIPTION OF THE PREFERRED EMBODIMENTS

The present invention relates to a catheter valve for use with a catheter. The catheter valve comprises an inlet nozzle at a front end of the valve and an outlet nozzle at a rear end of the valve. In particular, the valve comprises a longitudinal stem encapsulated within a middle section of the valve extending in between the front end and the rear end of the valve. The structural configuration of the longitudinal stem facilitates rapid inflation and deflation of an inflatable balloon at a distal end of the catheter during catheterization. Hereinafter, this specification will describe the present invention according to the preferred embodiments. It is to be understood that limiting the description to the preferred embodiments of the invention is merely to facilitate discussion of the present invention and it is envisioned without departing from the scope of the appended claims.

Figure 1:
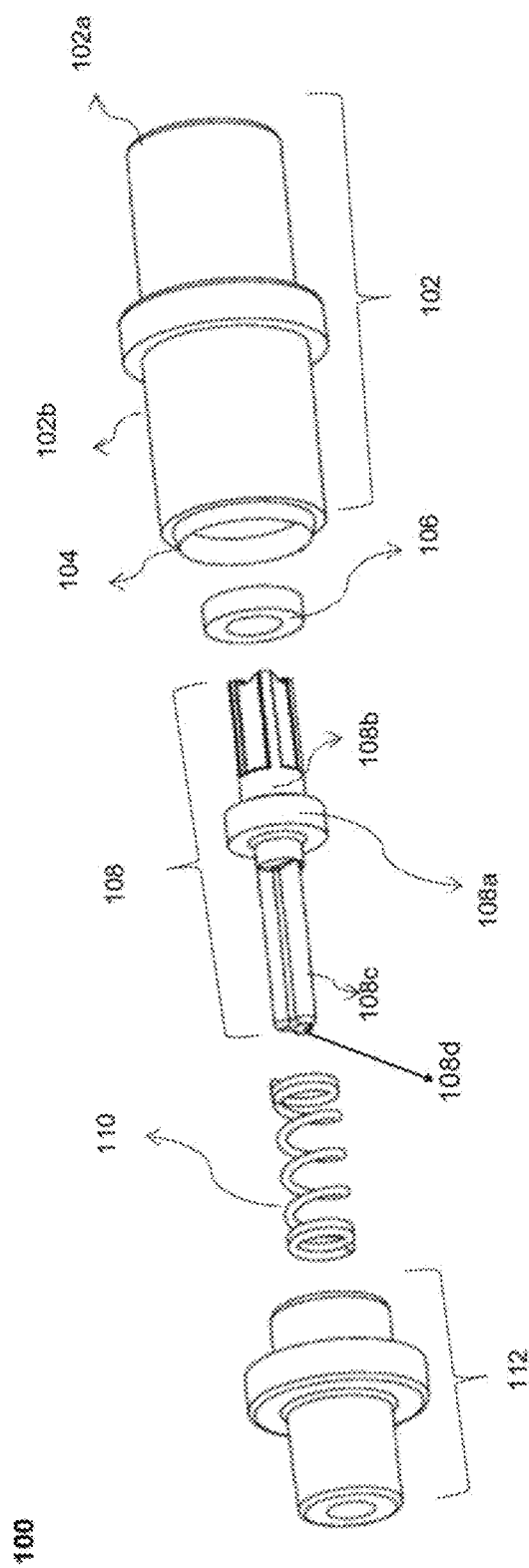
FIG. 1 illustrates an exploded view of an assembly of parts of the catheter valve of the present invention.
Figure 2:
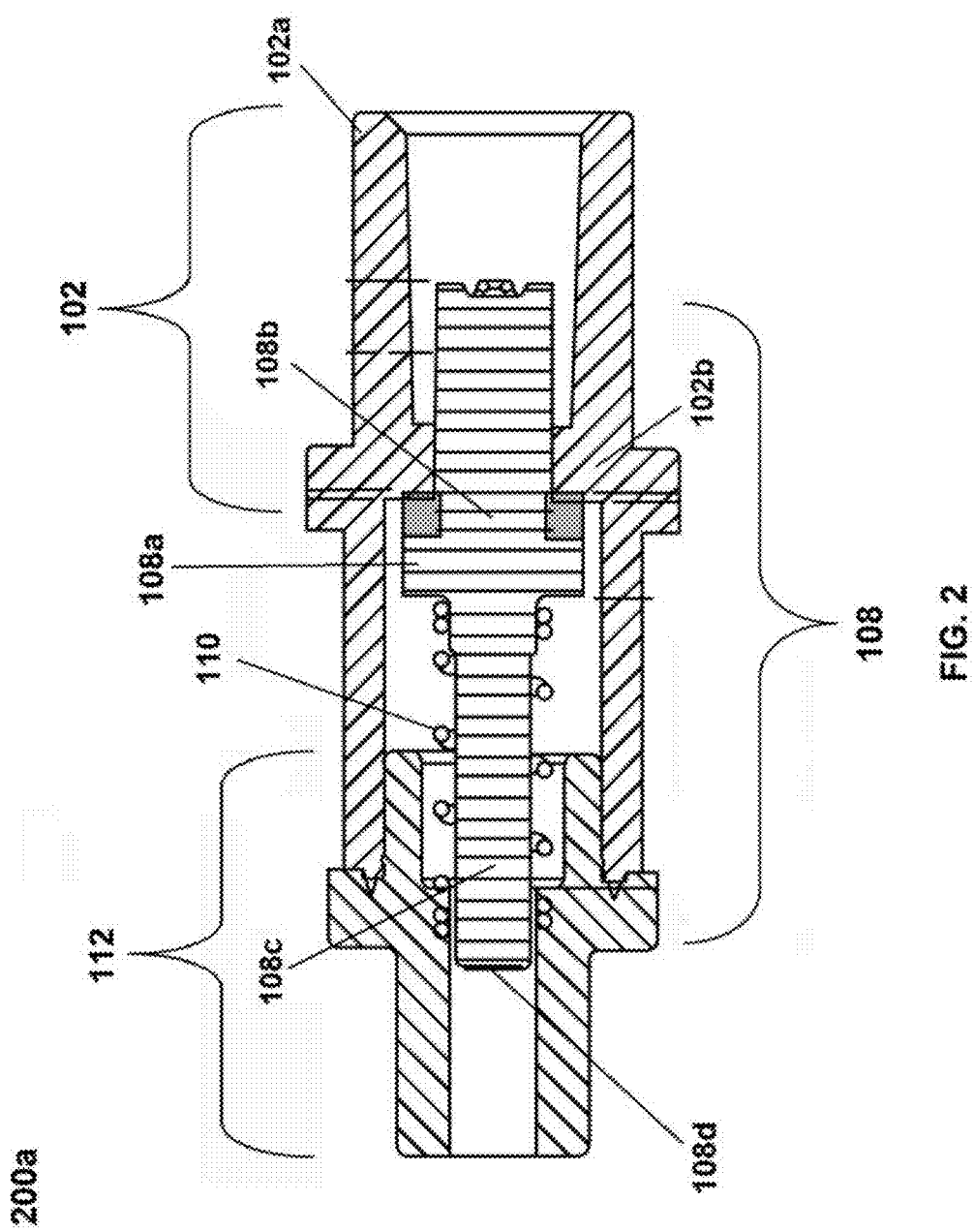
FIG. 2 illustrates a longitudinal cross sectional view of the catheter valve of the present invention.

Reference is first made to FIG. 1 and FIG. 2 simultaneously. FIG. 1 illustrates an exploded view of an assembly of parts of the catheter valve of the present invention and FIG. 2 illustrates a longitudinal cross sectional view of the catheter valve of the present invention. As illustrated in FIG. 1, the catheter valve (100) is made out of three main sections whereby the three main sections are namely a front end (102) of the valve (100) for receiving a syringe at an inlet nozzle (102a) to facilitate rapid inflation and deflation of an inflatable balloon at a distal end of the catheter during catheterization; a rear end (112) of the valve (100) with an outlet nozzle (112b) at the rear end (112) of the valve being inserted into one of the catheter's lumen enabling inflation and deflation of an inflatable balloon at a distal end of the catheter during catheterization; and a middle section (102b) which extends in between the front end (102) and the rear end (112) of the valve (100). The catheter valve (100) is preferably made of a plastic material such as polypropylene.

During catheterization, the inlet nozzle (102a) at a front end (102) of the valve (100) received a syringe to facilitate rapid inflation and deflation of an inflatable balloon at a distal end of the catheter. The catheter valve (100) comprises of a two part assembly with a first part of the assembly comprising a front end (102) and a middle section of the valve and a second part of the assembly comprising a rear end (112) of the valve with the outlet nozzle (112b). The catheter valve (100) is detachable between the front end and the rear end of the valve (100) whereby an interlocking means is provided between the front end (102) and the rear end (112) of the valve. The interlocking means is construed through an opening at the middle section (102b) of the valve through a cylindrical rib (104) which interlocks the front end (102) and the rear end (112) of the valve. An outlet nozzle (112b) at a rear end (112) of the valve (100) is inserted into one of the catheter's lumen enabling inflation and deflation of the inflatable balloon of the catheter during catheterization.

A longitudinal stem (108) is encapsulated within a middle section (102b) of the valve (100) which extends in between the front end (102) and the rear end (112) of the valve. The longitudinal stem (108) is further divided into a front end (108b) and a rear end (108c) by a rib (108a) and an O-ring (106) is inserted into the front end (102) of the stem enabling the O-ring (106) to be seated in a groove and compressed during assembly between the front end (108b) and the rear end (102) of the valve (100) creating a seal at a top interface of the rib (108a). The O-ring (106) is preferably made of rubber, silicone or any material which enables formation of a seal at a top interface of the rib. The front end (108b) of the longitudinal stem (108) is preferably half of a length of the rear end (108c) of the longitudinal stem (108). A resilient means is inserted at the rear end (112) of the longitudinal stem (108) to provide compressibility. The resilient means (110) includes a spring, and any other elastic material.

In assembling the valve, the inlet nozzle (102a) at a front end (102) of the valve is smaller in diameter at a front opening of a proximal end of the inlet nozzle and with a larger diameter towards a rear opening of a distal end of the inlet nozzle (102a). The front opening of a proximal end of the inlet nozzle (102a) and the rear opening of a distal end of the inlet nozzle with a change of diameter there between forms a seat which engages the head end of the front end (108b) of the longitudinal stem (108) up till the rib (108a) with the front end (108b) of the longitudinal stem (108) protrudes out of the seat and the rib (108a) resting at the bottom interface of the seat. The longitudinal stem provides a free flow passageway with no contact to the internal wall of the middle section of the valve. A front opening of the rear end (112) of the valve (100) with a change of diameter there between forms a seat which engages the head end of the rear end (108c) of the stem with the head end of the rear end (108c) of the stem resting on an interface in a middle of the internal rear end (112) of the valve.

The front end (108b) of the longitudinal stem (108) further comprises sectional longitudinal grooves which cuts across the longitudinal and cylindrical stem extending from a head end of the front end of the stem up till the rib (108a) of the stem and the head end is curved inwardly in between each sectional longitudinal groove; and the rear end (108c) of the longitudinal stem (108) further comprises sectional longitudinal grooves which cuts across the longitudinal and cylindrical stem (108) in a triangular form (108d) extending from a head end of the rear end (108c) of the stem up till a bottom interface of the rib (108a). The configuration of the front end (108b) of the longitudinal stem and the rear end (108c) of the longitudinal stem provides rapid air flow with minimal air resistance.

The present invention provides an improved catheter valve whereby the design and configuration of the longitudinal stem provides facilitates rapid inflation and deflation of an inflatable balloon at a distal end of the catheter during catheterization with much reduced restriction of air to flow along the passageway of the valve to the catheter.

Unless the context requires otherwise or specifically stated to the contrary, integers, steps or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of steps, elements or integers. Thus, in the context of this specification, the term "comprising" is used in an inclusive sense and thus should be understood as meaning "including principally, but not necessarily solely".

The invention claimed is:

1. A catheter valve for use with a catheter comprising:
    an inlet nozzle at a front end of the valve for receiving a syringe to facilitate rapid inflation and deflation of an inflatable balloon at a distal end of the catheter during catheterization;
    an outlet nozzle at a rear end of the valve being inserted into one of the catheter's lumen enabling inflation and deflation of the inflatable balloon of the catheter during catheterization; and
    a longitudinal stem encapsulated within a middle section of the valve extending in between the front end and the rear end of the valve; the longitudinal stem is divided into a front end and a rear end by a rib; an O-ring is inserted into the front end of the stem enabling the O-ring to be seated in a groove and compressed during assembly between the front end and the rear end of the valve (100) creating a seal at a top interface of the rib; and a resilient means is inserted into the rear end of the stem;
    wherein,
    the front end of the longitudinal stem further comprises sectional longitudinal grooves which cut across the longitudinal and cylindrical stem extending from a head end of the front end of the stem up till the rib of the stem and the head end is curved inwardly in between each sectional longitudinal groove; and
    the rear end of the longitudinal stem further comprises sectional longitudinal grooves which cut across the longitudinal and cylindrical stem in a triangular form extending from a head end of the rear end of the stem up till a bottom interface of the rib.

2. The catheter valve according to claim 1, wherein the front end of the longitudinal stem is half of a length of the rear end of the longitudinal stem.

3. The catheter valve according to claim 1, wherein the inlet nozzle at a front end of the valve is smaller in diameter at a front opening of a proximal end of the inlet nozzle and has a larger diameter towards a rear opening of a distal end of the inlet nozzle.

4. The catheter valve according to claim 3, wherein the front opening of a proximal end of the inlet nozzle and the rear opening of a distal end of the inlet nozzle with a change of diameter there between forms a seat which engages the head end of the front end of the longitudinal stem up till the rib with the front end of the longitudinal stem protruding out of the seat and the rib resting at the bottom interface of the seat.

5. The catheter valve according to claim 1, wherein a front opening of the rear end of the valve with a change of diameter there between forms a seat which engages the head end of the rear end of the stem with the head end of the rear end of the stem resting on an interface in a middle of the internal rear end of the valve.

6. The catheter valve according to claim 1, wherein the middle section of the valve having an opening which connects to the rear end of the valve; the opening of the of the middle section of the valve further comprising a cylindrical rib which provides an interlocking means between the front end and the rear end of the valve.

7. The catheter valve according to claim 1, wherein the resilient means includes a spring.

8. The catheter valve according to claim 1, wherein the catheter valve is detachable between the front end and the rear end of the valve.

9. The catheter valve according to claim 1, wherein the catheter valve comprises a two part assembly with a first part of the assembly comprising the front end and the middle section of the valve and a second part of the assembly comprising the rear end of the valve with the outlet nozzle.

10. The catheter valve according to claim 1, wherein the O-ring is made of rubber, silicone or any material which enables formation of a seal.

11. The catheter valve according to claim 1, wherein the resilient means includes an elastic material that provides compressibility.

12. The catheter valve according to claim 8, wherein the catheter valve comprises of a two part assembly with a first part of the assembly comprising the front end and the middle section of the valve and a second part of the assembly comprising the rear end of the valve with the outlet nozzle.

13. A catheter valve for use with a balloon catheter comprising:
    an inlet nozzle at a front end of the valve for receiving a syringe to facilitate rapid inflation and deflation of an inflatable balloon at a distal end of the catheter during catheterization;
    an outlet nozzle at a rear end of the valve and having an outer diameter that facilitates insertion into a lumen of the catheter to enable inflation and deflation of the inflatable balloon of the catheter during catheterization; and
    a longitudinal stem encapsulated within a middle section of the valve extending in between the front end and the rear end of the valve; the longitudinal stem is divided into a front end and a rear end by a rib; an O-ring is inserted into the front end of the stem enabling the O-ring to be seated in a groove and compressed during assembly between the front end and the rear end of the valve (100) creating a seal at a top interface of the rib; and a resilient means is inserted into the rear end of the stem;

wherein, the front end of the longitudinal stem further comprises more than two spaced-apart, sectional longitudinal grooves which cut across the longitudinal and cylindrical stem and extend from a head end of the front end of the stem toward the rib of the stem, and wherein the head end is curved inwardly where each sectional longitudinal groove terminates; and the rear end of the longitudinal stem further comprises a total of three spaced-apart sectional longitudinal grooves which cut across the longitudinal and cylindrical stem and extend from a head end of the rear end of the stem toward a bottom interface of the rib, the rear end of the longitudinal stem having a triangular form.

\* \* \* \* \*